United States Patent [19]

Doi et al.

[11] Patent Number: 4,543,477
[45] Date of Patent: Sep. 24, 1985

[54] SAFETY DEVICE FOR DETECTING TROUBLE IN OPTICAL TRANSMISSION FIBERS

[75] Inventors: Yuzuru Doi; Masato Hara; Hideo Yoshihama, all of Tokyo, Japan

[73] Assignee: Asahi Kogaku Kogyo Kabushiki Kaisha, Tokyo, Japan

[21] Appl. No.: 477,311

[22] Filed: Mar. 21, 1983

[30] Foreign Application Priority Data

Apr. 19, 1982 [JP] Japan .............................. 57-56737[U]

[51] Int. Cl.⁴ ................................................ G02B 5/14
[52] U.S. Cl. ..................................... 250/227; 250/205; 356/73.1
[58] Field of Search ....................... 250/205, 227, 572; 128/303.1, 395; 219/121 EP; 356/237, 239, 73.1, 430; 350/96.1, 96.33; 372/6, 9

[56] References Cited

U.S. PATENT DOCUMENTS 3,981,592 9/1976 Williams .............................. 356/237
4,385,832 5/1983 Doi et al. ............................ 356/73.1

Primary Examiner—David C. Nelms
Assistant Examiner—J. Gatto
Attorney, Agent, or Firm—Hill, Van Santen, Steadman & Simpson

[57] ABSTRACT

A safety device for detecting troubles in an optical transmission fiber of a medical laser application to prevent accidents characterized by using either a laser light reflector from the exit end surface of the fiber or a secondary light. When trouble is detected, the safety device operates a mechanism for interrupting the coupling of a beam of laser light into the transmission fiber. The safety device includes an electrical circuit which allows appropriate use of the apparatus with the tip of the fiber in water or a physiological salt solution for treatment of a tumor in a urinary bladder. The electrical circuits will include amplifiers, comparators and logic circuits.

10 Claims, 3 Drawing Figures ately 0.8 to 1.3 seconds after the reflected light 7a has dropped to or below the level C, the A/D converter 15 receives a signal via the line 17 from the CPU 16 and sends a detection signal to the CPU 16 which in turn controls the operation of the laser light source 1 through the line 18 to prevent any additional laser light from being emitted from the source 1. Also, the shutter means 3 can be activated through the control line 19 to prevent any leakage of light from the source 1.

SAFETY DEVICE FOR DETECTING TROUBLE IN OPTICAL TRANSMISSION FIBERS

BACKGROUND OF THE INVENTION

The present invention relates to a safety device capable of detecting trouble in optical transmission fibers for a laser apparatus and particularly for a medical laser apparatus.

Heretofore, medical laser apparatuses producing a high power beam of laser light have been used conveniently with an endoscope for treatment of digestive organs or respiratory systems and generally for a surgical treatment. When an optical fiber or a bundle of fibers for transmitting such a beam of laser light of the laser apparatus are broken or their exit or incident end surfaces are damaged, a trouble-detecting device will detect the broken or damaged end surfaces and stop the continuation of the beam of laser light.

However, when the laser apparatus is used to treat a tumor in a urinary bladder, a physiological salt solution to cauterize the tumor is present. Thus, the reflectivity at the exit end surface of the single optical fiber or fibers will be vastly decreased because the surface or surfaces are immersed in the solution or in another liquid such as water. The result is that this reduction in reflectivity creates a false signal of a trouble state or condition and the false signal is detected to stop the operation of the laser apparatus in spite of the fact that the apparatus is operating in a normal condition.

SUMMARY OF THE INVENTION

Accordingly, it is an object of the present invention to provide a safety device which is used with a medical laser apparatus and immediately detects any trouble such as a breakage of the tip of an optical fiber or damage of one or more fibers if it occurs and which device allows an appropriate operation of the laser apparatus with a tip in water or a water solution for treatment of bladder tumors.

This object is accomplished by providing a safety device for the laser apparatus which comprises a hollow tube having an open end; a transmission fiber having an incident end surface and an exit end surface, said fiber extending into the hollow tube with the exit end surface being adjacent the open end; laser light source for emitting the beam of laser light; optical means for focusing the beam of laser light onto the incident end surface of the transmission fiber; control means for interrupting the beam of the laser light; and blast means for blowing air in the space between the tube end of the fibers. The improvement comprises a safety device having detecting means capable of detecting either the laser light reflector from the exit end surface of the fiber or a secondary light signal and actuating means to operate the control means in response to either signal to interrupt the beam of the laser light. In one aspect of the present invention, only the secondary light is used for operating the control means.

Other objects, advantages and features of the invention will be apparent from the following description of the preferred embodiment taken in conjunction with the accompanying drawings.

DETAILED DESCRIPTION OF THE PREFERRED EMBODIMENT

Figure 1:
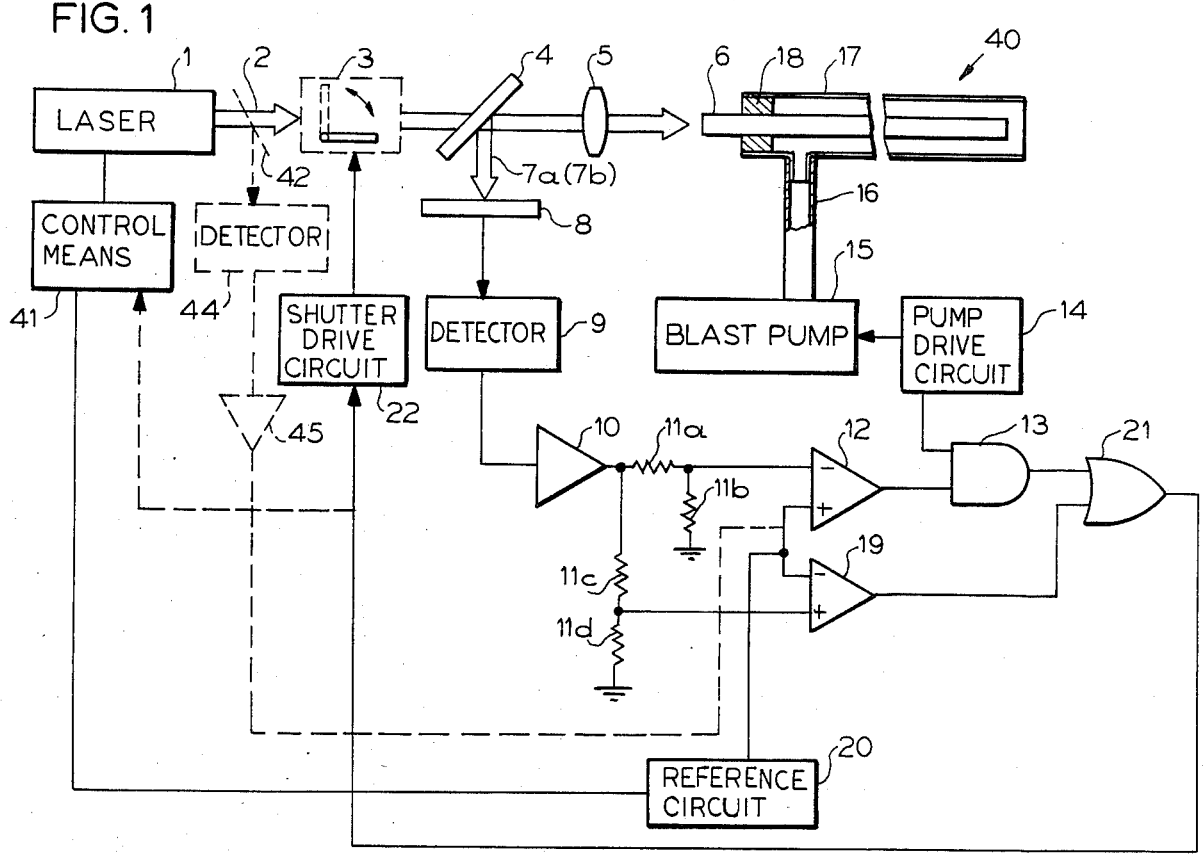
FIG. 1 is a schematic representation, partly in block diagram, of a medical laser apparatus equipped with a safety device embodying the concept of the present invention.

The principles of the present invention are particularly useful when incorporated in a medical laser apparatus generally indicated at 40 and schematically illustrated in FIG. 1. The apparatus 40 includes a laser light source 1 such as a Nd-YAG laser or a CO laser. The source 1 emits a beam 2 of laser light which beam passes through shutter means 3 of a control means which shutter means is disposed across the optical path. After passing through the shutter means, the beam 2 is transmitted through a transmission mirror 4. The light beam is then focused on the incident end surface of an optical fiber 6, which has either a polymer coating or a cladding layer of resinous material, by optical means comprising a condenser lens 5 and is transmitted through the fiber and thereafter it is directed to the diseased part of a patient from an exit end surface of the fiber 6.

A detection mechanism for detecting trouble in the fiber 6, if it exists, operates a safety mechanism by sensing the power or intensity of any laser light 7a which is reflected from the exit end surface of the fiber 6 and a secondary light 7b. Specifically, even when the apparatus operates normally, a slight portion of the beam 2 is reflected from the exit end surface of the fiber and is returned to the incident end. In a case where the exit end surface of the fiber is damaged or the incident end surface 6 is out of alignment with the optical axis of the lens 5, the reflected light 7a transmitted back to the incident end is attenuated. Consequently, it is possible to sense trouble in the fiber 6 by detecting changes in the amplitude or intensity of the reflected light. Also, in the situation where the fiber 6 is broken at a position between both ends or the exit or incident ends of the fiber are damaged, a faulty spot causes scattering and reflection of the beam 2 of laser light so that a portion of the cladding or polymer coating material which covers the fiber 6 near the faulty spot will burn and thus emit the aforementioned secondary light. A detection of the secondary light also enables one to discover trouble in the fiber 6. The detection mechanism as described hereinafter detects the changes in the reflected light 7a and detects any of the secondary light 7b to operate the safety mechanism or device.

It is now assumed that trouble as described above has occurred and that the reflected light 7a and secondary light 7b are emitted from the incident end of the fiber 6. The lights 7a and 7b pass through the condenser lens 5 and then a percentage of each transmitted light is reflected by the transmission mirror 4. It should be understood that any transmission mirror will reflect a small percent of the light projected thereon. Each reflected portion of the light then passes through a filter 8 which balances the light 7a with the secondary light 7b, then each of the lights 7a and 7b are received by a detector 9 which may be a phototransistor or a photodiode. In this example, the filter 8 absorbs a portion of the reflected light 7a but admits as much as possible of the secondary light 7b. This brings the energy levels of both types of light within the detection range of the detector 9.

The detector 9 converts the reflected light 7a into an electrical signal and the secondary light 7b into an electrical signal which signals are amplified by an amplifier 10. The amplified signals are supplied to an input terminal of a first solarity of a comparator 12 in a voltage dividing ratio determined by resistances 11a and 11b and to an input terminal of opposite polarity of a comparator 19 in a voltage dividing ratio determined by resistances 11c and 11d.

Figure 3:
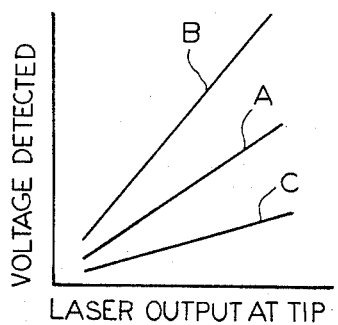
FIG. 3 is a graph of detected voltages versus output at the tip of the fiber with curve A being reference voltage levels, curve B being upper limit voltage levels and curve C being lower limit voltage levels.

The other input terminal of each of the comparators 12 and 19 is connected to a reference circuit 20 which generates a reference voltage whose value is shown by curve A in FIG. 3. The reference voltage level is the same as the voltage level of the reflected light 7a when the fiber is in a normal condition and will depend on the output of the laser source 1. As illustrated, the reference circuit 20 receives an output from a control means 41 for the laser source 1. In an alternative construction, a half mirror 42 shown in broken lines can be interposed between the light source 1 and the shutter means 3 to partially reflect a portion out of the optical path. The reflected portion is then received by a light-receiving device 44 which will convert into an electrical signal which is then amplified by an amplifier 45. The output of the amplifier 45 is applied to the input terminals of the comparators 12 and 19 as the reference voltage. Thus, as the output of the laser increases, the voltage will also increase as shown by curve A.

The output terminal of the comparator 12 which acts as a portion of the means for detecting and creating a first output is connected to one input terminal of an AND circuit 13. The other input terminal of this AND circuit 13 is connected to a pump drive circuit 14, which will energize and deenergize a blast pump 15 when the circuit 14 is switched on and off respectively. The drive circuit 14 may consist of only a mechanical or electrical switch in its simplest form. The pump 15 acts to blow air through a tube 16 connected to a hollow pipe or tube 17 with an open end. As illustrated, the fiber 6 extends into the hollow pipe 17 with the exit end surface being positioned slightly inward of the open end of the pipe 17. Thus, air received in the tube 16 flows between the hollow tube 17 and the fiber to be expelled at the open end. The other end of the pipe 17 is closed by a seal 18 which extends in the gap between the tube 17 and fiber 6.

The output terminal of the AND circuit 13 is connected to one input terminal of an OR circuit 21. The output terminal of the comparator 19 is connected to the other input terminal of the OR circuit 21. The output terminal of the OR circuit 21 is connected to a shutter drive circuit 22 which coacts with the shutter means to form the control means to interrupt the beam 2 of laser light. Thus, when the OR circuit 21, which will act as part of the actuating means, receives an output signal from either the comparator 19 or the AND circuit 13, it will actuate the drive circuit 22 which may include a solenoid which is actuated by the output from the OR circuit 21, and which circuit 22 will actuate the shutter means 3.

The operation of the apparatus 40 is as follows. It is assumed now that the beam 2 of laser light has been radiating without noticing that the fiber 6 is broken at a position between the two ends. Scattering and reflection of the light beam 2 would occur at this position of the break and result in burning of the resinous clad material or the coating of polymer that will cover the fiber 6. As a result, a secondary light 7b would be produced. In a situation where the exit end of the fiber 6 comes into contact with a target organ or comes too close to it, the exit end may also become too hot and thus generate a secondary light 7b.

Regardless of how the secondary light 7b is generated, it will be emitted from the incident end surface of the fiber 6 and pass through the lens 5. Then a portion will be reflected by the mirror 4 and pass through the filter 8 and is received by the detector 9 which will convert the secondary light 7b into an electrical signal that is amplified by the amplifier 10. The amplified signal is applied to the one input of the comparator 19 in the desired voltage dividing ratio which is determined by the resistances 11c and 11d. Since the other input of the comparator 19 is supplied with a reference voltage from the reference circuit 20 or the alternate arrangement, the voltage derived from the secondary light 7b will be compared with the reference voltage level A. When it reaches a predetermined upper limit voltage illustrated by the curve B in FIG. 3, an output signal from the comparator 19 is applied to one input terminal of the OR circuit 21. This causes the circuit 21 to operate and supply an electrical signal to the drive circuit 22 whether the reflected laser light 7a is normal or attenuated. Then the circuit 22 will cause the shutter means 3 to close to thus block further propagation of the beam 2 into the fiber 6. Thus, the detector 9, amplifier 10 and comparator form first means for detecting and forming a first output received by the actuating means which include the OR circuit 21.

If the exposed core of the exit end of the fiber 6 is damaged or the incident end of the fiber 6 is out of alignment with the optical axis of the lens 5, then the reflected light 7a, which was reflected at the exit end surface and emitted from the incident end to pass through the lens 5 will be attenuated. The light 7a reflected from the mirror 4 then passes through the filter 8 and is received by the detector 9 which converts the light into an electrical signal that is amplified by the amplifier 10. The resultant signal is applied to one input of the comparator 12 and a voltage dividing ratio determined by the resistances 11a and 11b.

As the other input of the comparator 12 is supplied with a reference voltage such as from the circuit 20, the voltage of the reflected light 7a will be compared with the reference voltage and if it drops to a predetermined low limit voltage level such as shown by the curve C of FIG. 3, an electrical signal will be supplied from the output of the comparator 12 to one input of the AND circuit 13. Thus, the detector 9, amplifier 10 and comparator 12 form second means for detecting and creating a second output. In many operations, the drive circuit 14 for driving the blast pump 15 is usually energized so that the putrid matter given off from the diseased portion by the irradiaton of the beam 2 of laser light will not adhere to the exit end surface of the fiber 6. Accordingly, the electrical output signal from the drive circuit 14 will be applied to the other input of the AND circuit 13 which acts as third means which will then provide an electrical output signal or third output to the other input of the OR circuit 21. Thus, the circuit 21 will apply an electrical signal to the driver circuit 22 for energizing the circuit 22 even though the secondary light 7b was not generated. In this way, the shutter means 3 will be closed to prevent the further passage of the light beam 2.

When the laser apparatus is used with the exit end surface of the fiber in contact with water or other liquid such as during the treatment of a tumor in a bladder which is filled with a physiological salt solution or when contamination of the exit end surface of the fiber 6 is prevented or a bleeding portion is cleansed by means of a water-conveying mechanism instead of the blast mechanism using the pump 15, the driver circuit 14 is deenergized. Therefore, the circuit 14 will fail to apply a signal to the other input of the AND circuit 13. Consequently, even though there is no damage to the end surface and the fiber is operating in a normal condition, a marked decrease in reflectivity at the exit end surface of the fiber 6 will attenuate the reflected light 7a to allow the comparator 12 to apply an output signal to one of the inputs of the AND circuit 13. However, since the AND circuit 13 will not be receiving an input from the drive circuit 14, it will not create an output signal. Therefore, the only signal that will be applied to the OR circuit 21 is a signal from the comparator 19 which is created when a secondary light 7b has been generated due to a defect as mentioned hereinabove. In this way, the aforementioned inconvenience of not being able to utilize the laser apparatus with the tip immersed in water or a salt solution due to the creation of false signals is eliminated.

Figure 2:
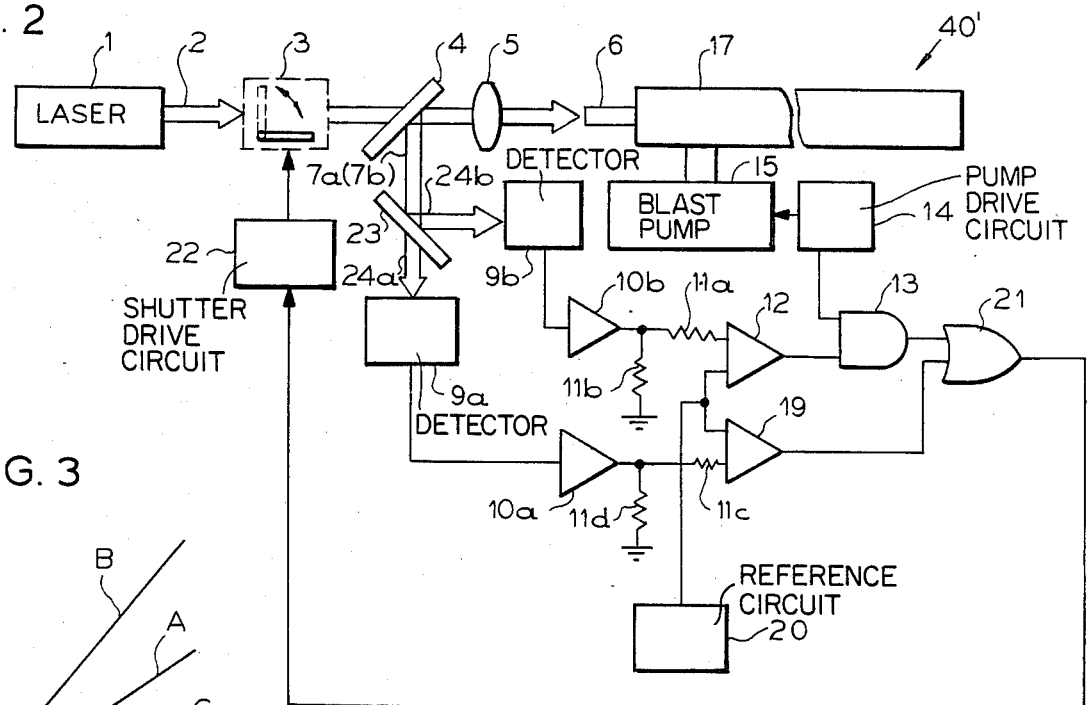
FIG. 2 is a schematic representation, partly in block diagram, of a medical laser apparatus equipped with another embodiment of the safety device of the present invention.

The laser apparatus generally indicated at 40' is schematically illustrated in FIG. 2. Basically, the apparatus 40' is very similar in operation to the apparatus 40 except for the following different features. The reflected light 7a and the second light 7b which are emitted from the incident end suface of the fiber 6 are reflected by the mirror 4 onto a mirror 23 which will separate the two lights into a separate secondary light portion 24a which is received by a detector 9a that will convert the light into an electrical signal that is amplified by amplifier 10a. In a similar manner, a portion 24b which was separated by the mirror 23 by being reflected thereby is received by a detector 9b which will convert the light into an electrical signal that is amplified by an amplifier 10b. In a manner of the previous description of the apparatus 40, the output of the amplifer 10a is connected to a comparator 19 while the output of the amplifier 10b is connected to an input of a comparator 12. The outputs of the two comparators 12 and 19 are applied in the same manner to the AND circuit 13 and the OR circuit 21 as in the previous embodiment. Thus, the first means comprises the detector 9a, amplifier 10a and comparator 19 while the second means is formed by the detector 9b, amplifier 10b and comparator 12.

In both the above described embodiments, the OR circuit 21 functions to operate the shutter drive circuit 22 in order to close the shutter means 3 to interrupt the beam 2. In an alternative manner, the OR circuit 21 can act to apply an electrical signal to the control means 41 or drive circuit for the laser light source 1 to turn off the laser. Thus, the control means 41 when receiving a signal from the OR circuit 21 can operate a switch on the power supply for the laser to turn it off.

The apparatus constructed as described hereinabove can prevent any accident by the high powered beam of laser light which is emitted from a medical laser apparatus by detecting trouble such as breakage of the optical fiber or fibers which are used to transmit the beam of laser light or damage on the end surface of the fiber or fibers immediately after it has occurred. Further, the novel apparatus can prevent erroneous detection of the fiber condition which would have been heretofore encountered in situations where urinary organs are treated or water jets are utilized so that the tip of the fiber may not be contaminated or a bleeding portion may be cleaned. In addition, the novel apparatus is quite simple in construction and therefore any substantial alteration is not necessary to the incident portion of the laser fibers of the prior art apparatus when utilized with the present invention. Thus, the novel apparatus or detecting device is quite practical in that it can be economical to fabricate and furthermore it insures safety in medical laser applications.

Although various minor modifications may be suggested by those versed in the art, it should be understood that we wish to embody within the scope of the patent granted hereon, all such modifications as reasonably and properly come within the scope of our contribution to the art.

We claim:

1. In a safety device for detecting trouble in an optical transmission fiber of a medical laser apparatus, the laser apparatus comprising a hollow tube having an open end; a transmission fiber having an incident end surface and an exit end surface, said fiber extending into the hollow tube with the exit end surface being adjacent the open end; a laser light source for emitting a beam of laser light; optical means for focusing the beam of laser light onto the incident end surface of the transmission fiber; control means for interrupting the beam of laser light; and blast means for blowing air in the space between the tube and the fiber, the improvements comprising a safety device having detecting means capable of detecting both the laser light signal reflected from the exit end surface of the fiber and a secondary light signal and actuating means to operate the control means in response to detection of either the secondary light signal or the laser light signal and the signal from an operating blast means.

2. The improvements according to claim 1, wherein said blast means causes said actuating means to respond only to the secondary light signal upon deactivation of said blast means.

3. In a safety device for detecting trouble in an optical transmission fiber of a medical laser apparatus, the laser apparatus comprising a hollow tube having an open end; a transmission fiber having an incident end surface and an exit end surface, said fiber extending into the hollow tube with the exit end surface being arranged adjacent the open end; a laser light source for emitting a beam of laser light; optical means for focusing the beam of laser light onto the incident end of the transmission fiber and control means for interrupting the beam of laser light, the improvement comprising a safety device having first means for detecting a secondary light signal in the transmission fiber and creating a first output, actuation means for receiving the first output and operating the control means to stop the beam of laser light from being received in the transmission fiber.

4. The improvements according to claim 3, wherein said apparatus includes blast means for blowing air in the space between the fiber and the hollow tube and for creating a signal when operating, and said device includes second means for detecting a laser light signal reflected from the exit end surface and for creating a second output, third means for receiving the second output and the signal from said blast means and for creating a third output which is applied to the actuation means, said actuation means operating the control means when the third output is received so that the control means are operated to stop the laser beam when either the laser signal reflected from the end surface or the secondary light signals are received.

5. The improvement according to claim 4, wherein said control means comprise a shutter means disposed in the optical path of the beam of laser light between the optical means and the source to block the optical path.

6. The improvement according to claim 4, wherein said control means comprise a switch means to shut off the source of laser light.

7. The improvement according to claim 4, wherein the third means is an AND circuit.

8. The improvement according to claim 4, wherein said actuating means include an OR circuit.

9. The improvement according to claim 3, wherein the control means is shutter means for blocking the optical path of the beam as it leaves the source.

10. The improvement according to claim 3, wherein the control means include a switch in the power supply for the source.

* * * * *